United States Patent
Herrmann et al.

(10) Patent No.: US 6,543,274 B1
(45) Date of Patent: Apr. 8, 2003

(54) SENSOR ARRAY AND METHOD FOR DETERMINING THE DENSITY AND VISCOSITY OF A LIQUID

(75) Inventors: Falk Herrmann, Leonberg (DE); Dietmar Hahn, Gerlingen (DE); Gottfried Flik, Leonberg (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/830,597

(22) PCT Filed: Sep. 22, 1999

(86) PCT No.: PCT/DE99/03023
§ 371 (c)(1),
(2), (4) Date: Apr. 27, 2001

(87) PCT Pub. No.: WO00/26658
PCT Pub. Date: May 11, 2000

(30) Foreign Application Priority Data

Nov. 4, 1998 (DE) .......................................... 198 50 803

(51) Int. Cl.⁷ ........................... G01N 9/00; G01N 11/10
(52) U.S. Cl. ..................... 73/32 A; 73/54.41; 73/24.05
(58) Field of Search ........................... 73/32 A, 290 R, 73/290 V, 32 R, 30.04, 54.14, 54.24, 54.25, 54.26, 54.32, 54.34, 54.41, 24.05, 30.01, 24.06, 31.05; 310/313 A, 313 R

(56) References Cited

U.S. PATENT DOCUMENTS 5,130,257 A * 7/1992 Baer et al. ................. 73/DIG. 4
5,741,961 A    4/1998 Casaus
5,992,215 A * 11/1999 Caron et al. ................ 73/24.01
6,247,354 B1 * 6/2001 Vig et al. ................... 73/54.41
6,269,686 B1 * 8/2001 Hahn et al. ................. 73/54.24
6,378,370 B1 * 4/2002 Haskell et al. .............. 73/24.06
6,407,479 B1 * 6/2002 Moellendorf et al. ... 310/313 A

FOREIGN PATENT DOCUMENTS

WO       87 02134 A      4/1987

OTHER PUBLICATIONS

1993 IEEE International Frequency Control Symposium, Measuring Liquid Properties with Smooth– and Textured –Surface Resonators, by S. J. Martin et al, pp. 603–608, Mar. 1993.
Du J. et al: "A Study of Love–Wave Acoustic Sensors", Sensors and Actuators, vol. A56, No. 3, Sep. 1, 1996, pp. 211–219.
Patent Abstract of Japan vol. 1999, No. 13, Nov. 30, 1999, No. 13 & JP 11 211705 A, Aug. 6, 1999.
H. Baltes et al., Sensors–Update, vol. 2, pp. 42–47 and 62–65, VCH–Verlagsgesellschaft, 1996.

* cited by examiner

*Primary Examiner*—Helen Kwok
(74) *Attorney, Agent, or Firm*—Michael J. Striker

(57) ABSTRACT

A sensor arrangement for ascertaining the density and the viscosity of a liquid is proposed, having an arrangement comprising at least two basic sensor elements, at least one of which can be wetted with the liquid, and having electro-acoustical transducers (6) in the basic sensor elements for generating and detecting surface acoustic waves with pre-determined wave modes, from whose propagation behavior along a measurement path a measure for the density and the viscosity of the liquid can be ascertained. Liquid traps (17) for the liquid, which extend in the applicable measurement path, are disposed in the region of at least one of the basic sensor elements, parallel to the direction of propagation of the surface acoustic wave.

15 Claims, 4 Drawing Sheets

SENSOR ARRAY AND METHOD FOR DETERMINING THE DENSITY AND VISCOSITY OF A LIQUID

PRIOR ART

Figure 1:
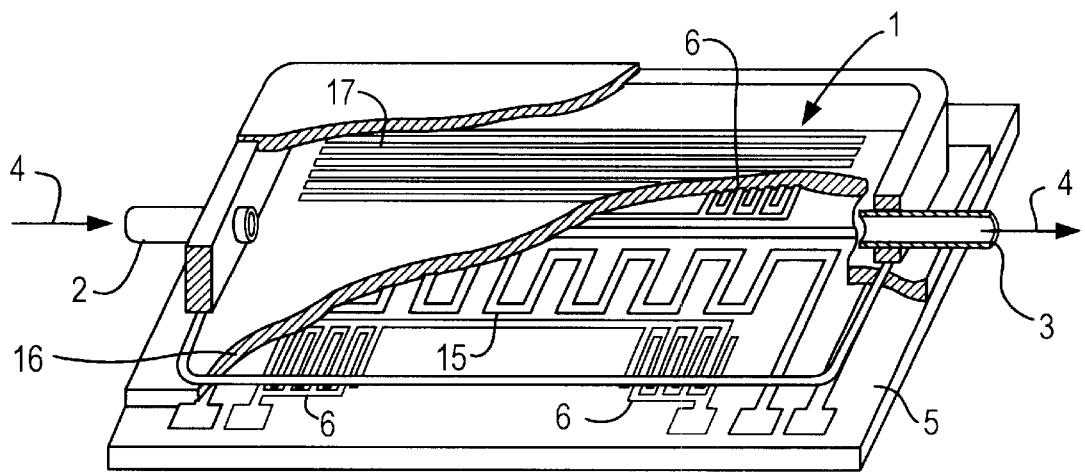

The invention relates to a sensor arrangement for ascertaining the density and viscosity of liquids, and to a method for performing this ascertainment, as generically defined by the preamble to the main claim.

In general, in a density measurement the mass of a known volume of liquid is ascertained using simple measurement arrangements. In addition, the resonance mistuning can be ascertained and evaluated to determine the density in a tube, through which the examined liquid flows, in an acoustical measurement arrangement. Well-known measuring methods that can be used to measure the viscosity of the liquid are rotation viscosimetry and trap ball viscosimetry. It is common to all the methods named that the two measurement variables of density and viscosity must be ascertained using different apparatuses, which each require a great deal of space, are cost-intensive when there is a demand for high measurement precision, and require relatively large liquid volumes for the measurement.

In view of an ever-increasing necessity for miniaturization and system integration, there is a need for compact, cost-effective apparatuses for high-precision on-line density and viscosity measurement in small volumes of liquid, but this need cannot be met with the measurement apparatuses available today. Examples of such an application are measuring the density and viscosity when metering diesel fuels in motor vehicles, on-line monitoring of the status of motor oils, or the development of microfluidic analysis systems in chemistry or medicine, for example for studying such physiological media as blood or urine, or for producing pharmaceutical products.

Microsensors for density and viscosity measurement of liquids can be classified in two categories, in accordance with their fundamental functional principles. The first is so-called surface acoustic wave sensors (SAW sensors), which work by using an interaction between the propagation path of a surface acoustic wave or a bulk wave and the liquid to be studied, and the second is sensors whose measuring transducers comprise resonantly vibrating microstructures.

In the sensor arrangement of the generic type involved here, the point of departure is a known measurement principle that is described for instance in the article entitled "A study of Love-wave acoustic sensors", J. Du, G. L. Hardling, P. R. Ogilvy and M. Lake, in the professional journal Sensors and Actuators A56 (1996), pages 211–219. With the measurement layout described here, a sensor is realized in which work is done with horizontally polarized acoustic shear waves as surface waves, that is, so-called leaky waves or surface skimming bulk waves (SSBWs), or Love waves. These acoustic wave modes are generated and also detected with so-called interdigital transducers, known per se from the aforementioned prior art, so that from the propagation behavior along a propagation or measurement path, the desired sensor signal can be obtained.

ADVANTAGES OF THE INVENTION

The sensor arrangement of the applicable generic type recited at the outset for ascertaining the density and the viscosity of a liquid is advantageously refined in accordance with the invention as defined by the characteristics of the body of the main claim and the coordinate method claim.

This sensor arrangement according to the invention, by utilizing the influence of additional interferences, imposed in a targeted way on the sensor surface of a basic sensor element, in a propagation path for the acoustic waves advantageously enables a separate measurement of density and viscosity of a liquid in a measurement layout with high measurement precision. In the known arrangement referred to at the outset, conversely, in a measurement using Love wave modes, it is possible only to detect a density-viscosity product.

Per se, a viscosity and density sensor with a so-called quartz crystal microbalance (QCM) for measurement with bulk waves, rather than surface waves, is known in which similar interferences are provided in the form of liquid traps. This is described for instance in the paper entitled "Measuring Liquid Properties with Smooth-and Textured-Surface Resonators", by S. J. Martin et al, IEEE 1993 International Frequency Control Symposium, pages 603–608. Here the surface of the one oscillator, for instance, is provided with walls of metal, such as gold, that are oriented perpendicular to the direction of oscillation. The pockets between the walls act as liquid traps, and the liquid located therein executes the oscillation motion regardless of its viscosity.

This known quartz crystal microbalance is a thickness shear oscillator, which is excited by low electrodes, utilizing the inverse piezoelectric effect. Since in a liquid phase, because of the shear motion, no direct projection of acoustical energy occurs, because shear modes are not capable of propagation in liquids, the QCM is suitable for studying liquids as well. Often, a change in resonant frequency is measured by mass accumulation, and the QCM acts as a frequency-determining element in an oscillator circuit.

The invention advantageously exploits the effect that in viscous liquids, because of viscous coupling, a frequency shift dictated by the viscosity and density of the liquid additionally occurs. This can be used to ascertain the density-viscosity product of the liquid, but in addition the influence of density from the influence of viscosity can be distinguished with the layout proposed according to the invention, so that both variables can be measured independently of one another.

Thus in a refinement of the generic arrangement, at least two basic sensor elements, operated parallel in terms of their construction, are advantageously used, and the advantages of using surface waves, especially SSB waves or Love waves, can be exploited. These advantages are above all a high measurement sensitivity, the use of transducer electrodes that are protected from the liquid, an inert surface, and low cross sensitivity.

Compared to the use of the known QCMs, in the arrangement of the invention the application of gold by electroplating can be dispensed with, and the entire sensor arrangement can be produced in a semiconductor-compatible production process. Since the gold used in the known arrangement with QCMs has a very high density compared to the liquid, with the layout according to the invention, whose materials are closer in density to that of the liquid, the measurement sensitivity can also be enhanced by comparison.

With the claimed measurement method, a measurement signal that is easy to process further can be obtained in a simple way by the evaluation of frequency shifts. The frequency shifts of the basic sensor element with the liquid traps, in addition to the influence of the density-viscosity product, has a dependency that is dictated only by the density of the liquid and by the effective volume of the liquid traps. If the frequency shifts of the two basic sensor elements are then linked together, the density and viscosity of the measurement liquid can be ascertained separately.

With the present invention, a microsensor is proposed, with which the determination of the density and the viscosity of volumes of liquid in the microliter range is possible with high resolution and high measurement precision. This sensor can be produced economically in batch processes that are suitable for mass production, with recourse to methods known from semiconductor manufacture. Thus the advantages of sensors which generate a measurement signal by utilizing the interaction between the propagation path of a surface acoustic wave and the liquid to be studied, and other sensors (such as bulk mode sensors or QCMs) can thus be combined, and the various specific disadvantages thereof are avoided.

These and further characteristics of preferred refinements of the invention are disclosed not only in the claims, including the dependent claims, but also in the specification and drawings; the individual characteristics can each be realized alone or in various subsidiary combinations in the embodiment of the invention and in other fields and can represent versions that are advantageous and are worthy of patent protection on their own, for which patent protection is here claimed.

DRAWING

Figure 2:
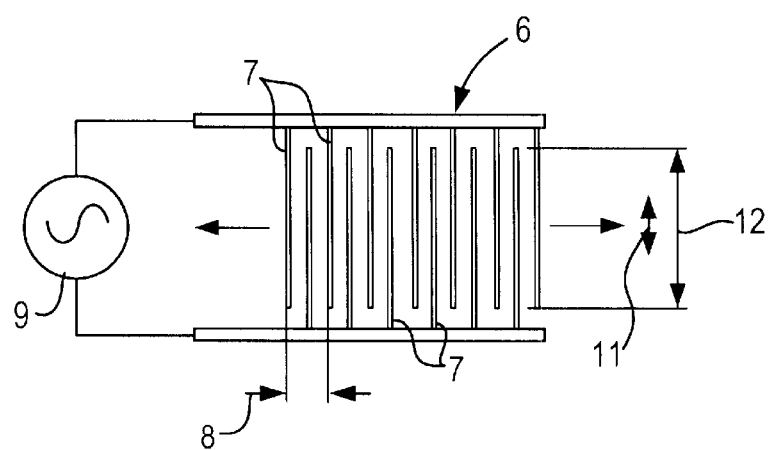
Figure 3:
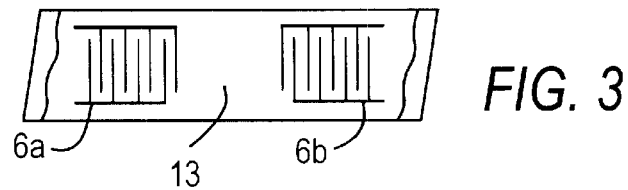
Figure 4:
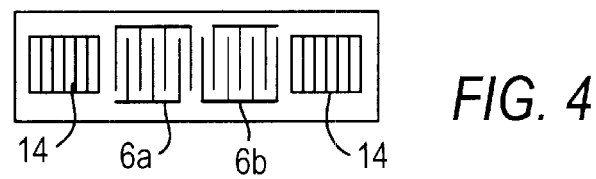
Figure 5:
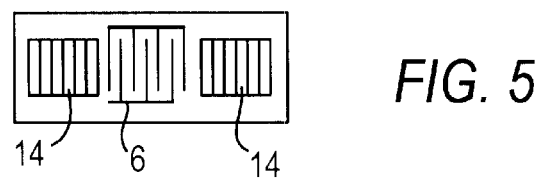
Figure 6:
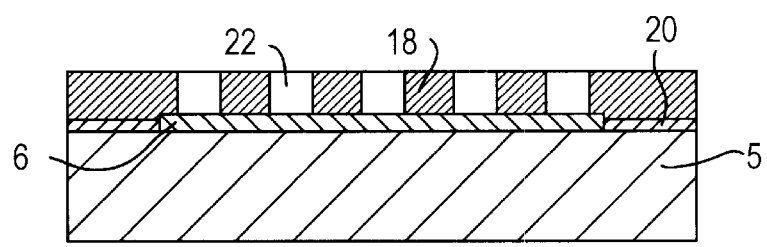
Figure 7:
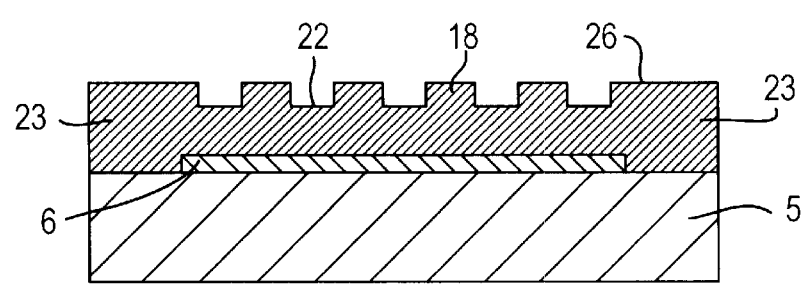
Figure 8:
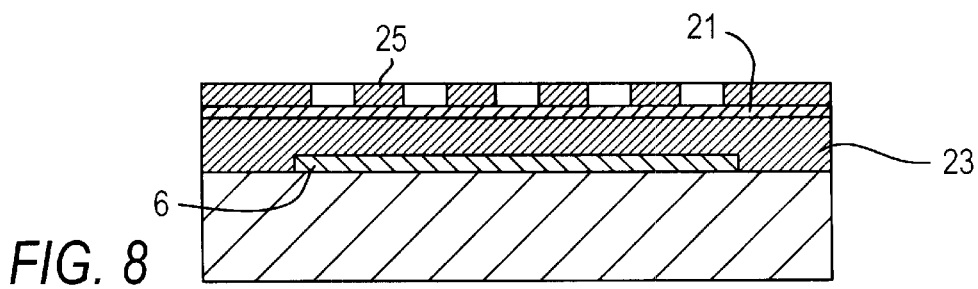
Figure 9:
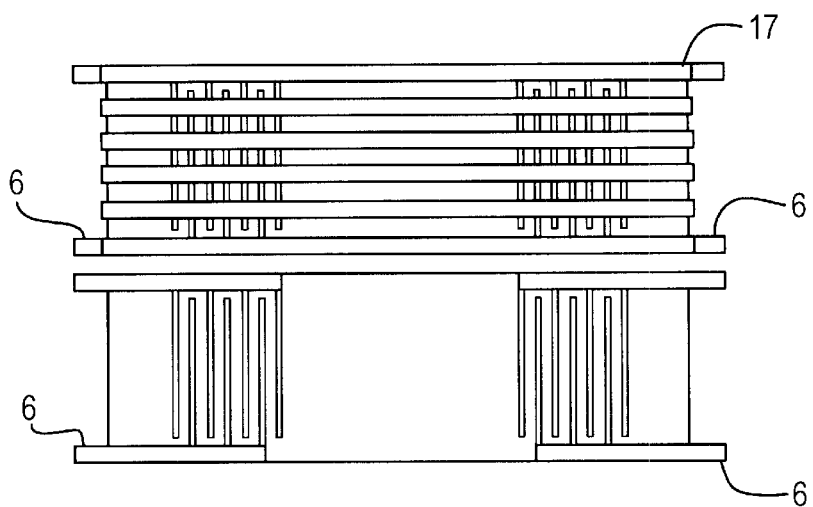
Figure 10:
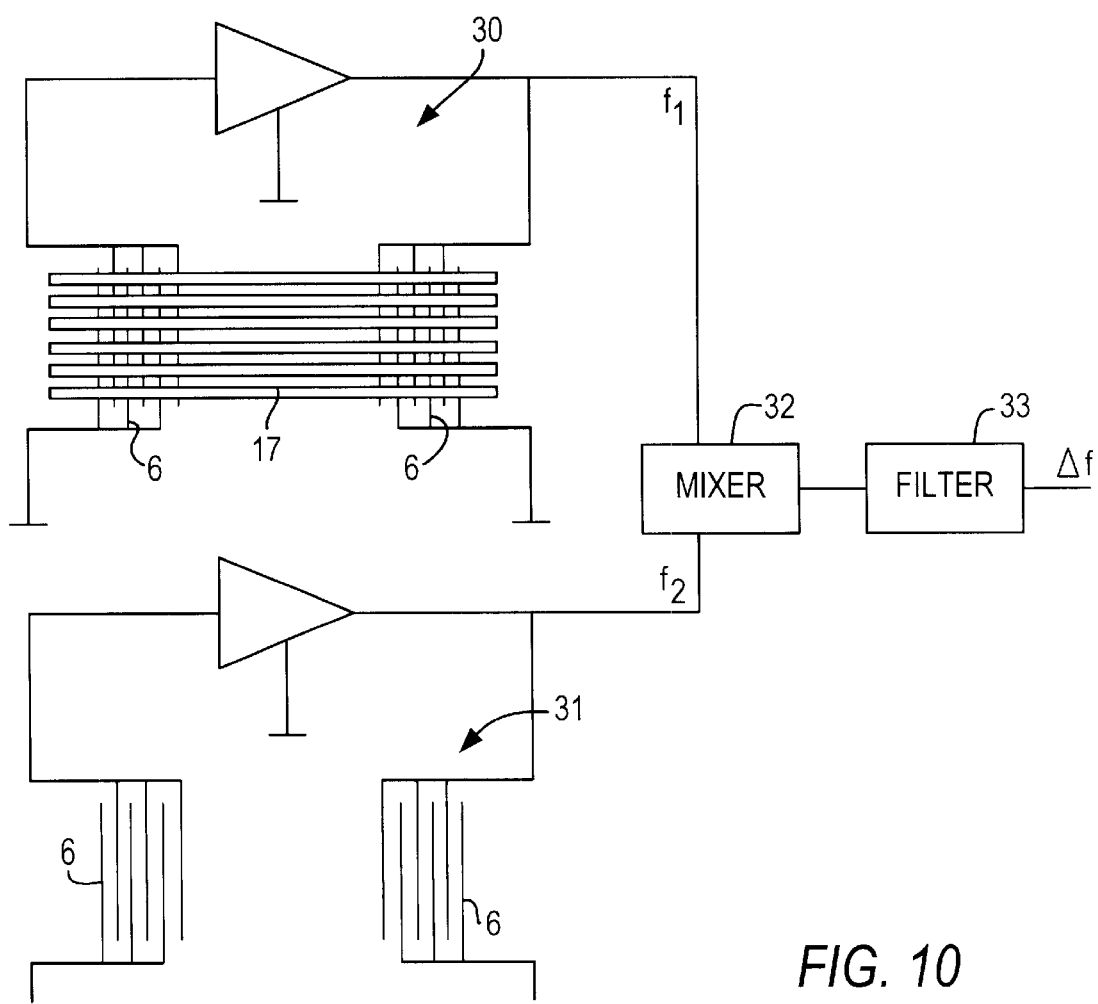
Figure 11:
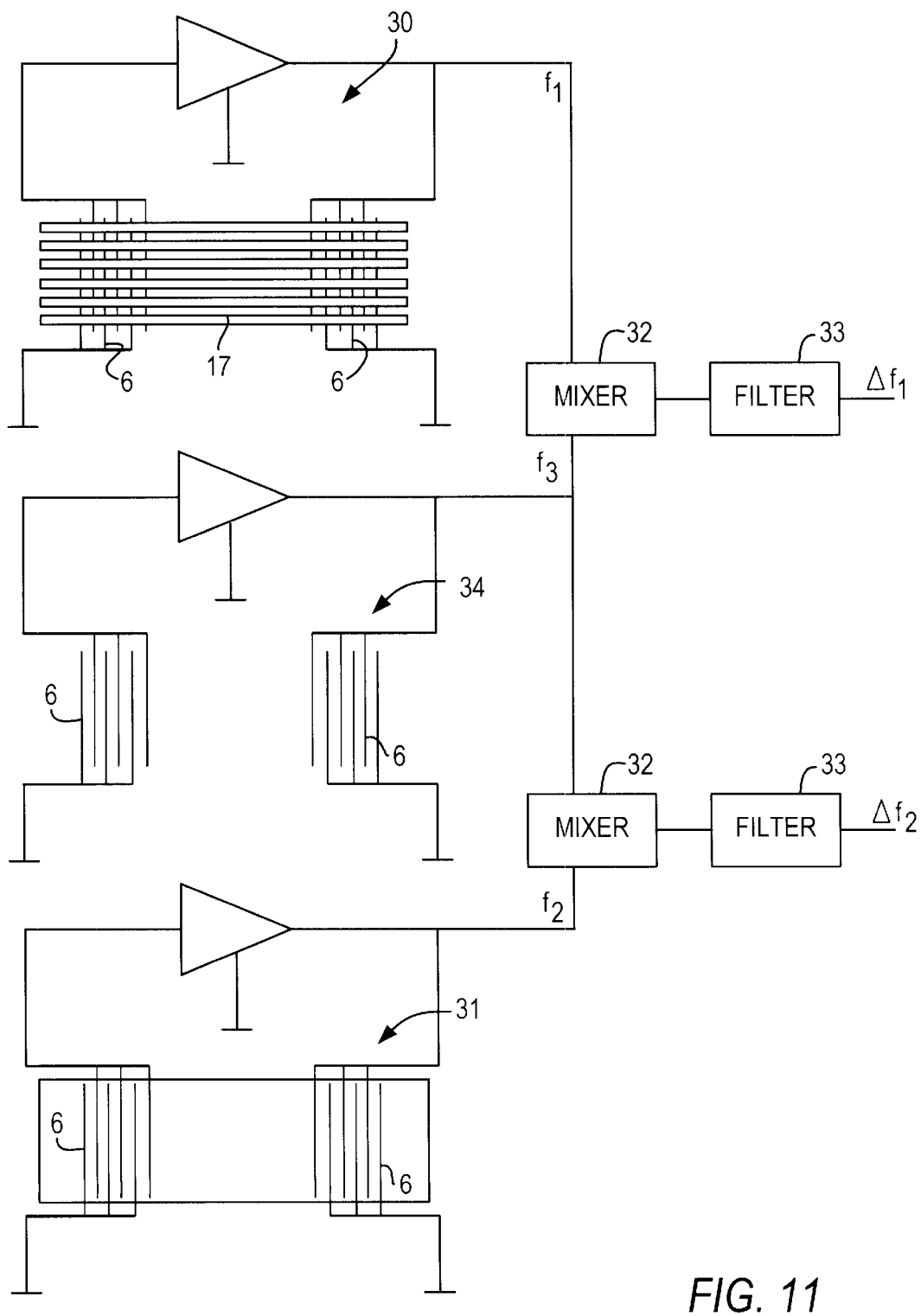

Exemplary embodiments of the sensor arrangement of the invention will be described below in conjunction with the drawing. Shown are:

FIG. 1, a schematic view of a sensor arrangement for ascertaining the density and the viscosity of a liquid flowing through the sensor arrangement;

FIG. 2, a detail of an interdigital transducer for generating and detecting acoustic waves;

FIGS. 3–5, variant arrangements of the interdigital transducer of FIG. 2;

FIGS. 6–8, sections through a substrate of the sensor arrangement, with different versions of the coating;

FIG. 9, a more-detailed plan view of two propagation paths of the measurement liquid in the sensor arrangement;

FIG. 10, a basic circuit diagram of an evaluation circuit coupled to the sensor arrangement; and FIG. 11, an evaluation circuit that is expanded compared to FIG. 10.

DESCRIPTION OF THE EXEMPLARY EMBODIMENTS

In FIG. 1, a sensor arrangement 1 is shown in a basic cutaway view; a measurement fluid flows through this arrangement from an inlet 2 to an outlet 3 in the direction of the arrow 4, so that its density and viscosity can be determined. The primary component of the proposed sensor arrangement 1 is a substrate 5, polished on one side, of a piezoelectric material in which horizontally polarized acoustic shear waves can be excited by basic sensor elements and are capable of propagation. As substrate materials, Y-rotated quartz slices, some lithium niobate and lithium tantalate slices, and correspondingly polarized piezoelectric ceramics are suitable.

Located on the polished surface of the substrate 5 is an arrangement of metal interdigital transducers (IDTs) 6, which will be explained in further detail in conjunction with FIG. 2. These interdigital transducers 6 are for instance of aluminum, titanium, chromium, gold or platinum, optionally on an adhesion layer of titanium or silicon, and serve to excite and detect the surface acoustic waves.

In FIG. 2, one of the interdigital transducers 6 is shown in detail; transducer prongs 7 are capable of generating acoustic waves at the wavelength 8 (medium frequency) upon excitation by an electrical voltage at an input 9. The result is a surface acoustic wave, that is, in particular a shear wave, in the polarization direction indicated by the arrow 11, with the aperture indicated by arrow 12. In an exemplary embodiment not shown here, the transducer prongs 7 can also be split within the period into two individual prongs or split prongs, thus creating $\lambda/8$ prongs. Between the electrical and the mechanical period is the factor of 2 in this case, so that it is possible for internal reflections and the so-called triple transit echo (TTE) to be eliminated or at least reduced.

The arrangement of the interdigital transducers 6 in the sensor arrangement 1 of FIG. 1 can be embodied in accordance with the exemplary embodiments of FIGS. 3–5. For instance embodied as a delay line with a transmitting IDT 6a, a propagation path 13 and a receiving IDT 6b, or in FIG. 4 as a two-gate resonator or in FIG. 5 as a one-gate resonator with one or two IDTs 6 and with reflector banks 14.

The sensor arrangement 1 of FIG. 1 includes two basic elements, disposed parallel to one another, with the interdigital transducers 6, but for the sake of simplified evaluation and improved temperature compensation of the measurement signals, a third parallel basic sensor element, not shown in this figure, can also be provided. Also in the exemplary embodiment of FIG. 1, next to or in between the basic elements with the IDTs 6 on the surface of the substrate 5, there is a thin-film temperature resistor 15 of meandering shape, since the viscosity in particular is highly temperature-dependent, and thus the temperature represents a further important measurement variable. As the material for the thin-film temperature resistor 15, the material as for the IDTs 6 can advantageously be considered, namely titanium/platinum or titanium/platinum/titanium, and the adhesion layer can be either titanium or silicon.

On the substrate 5 of FIG. 1, above the basic elements with the IDTs 6, an acoustic waveguide layer 16 is provided, which can for instance comprise an ormocer, a silicon compound, or a polymer, so that the general shear mode (leaky wave or SSBW) of the acoustic wave becomes a so-called waveguide mode (in this case, a Love wave). To distinguish the effect of density from the effect of viscosity in the measurement, mechanical interferences in the form of liquid traps 17 are intentionally disposed above the basic element having the IDTs 6, and inside these liquid traps, because of the mechanical discontinuity, the acoustic wave is incapable of propagation.

To that end, the region before, above and between the various interdigital transducers 6 is provided with the walls 18, oriented parallel to the direction of propagation of the acoustic wave, and the geometric options for the disposition of these walls will be explained in conjunction with FIGS. 6–8 and the plan view of FIG. 9. These liquid traps 17 can be produced here in the form of trenches 22, as shown in FIG. 6, or as pits or sponges, not shown, by suitable structuring of a layer 20 located above the interdigital transducer 6. Between the layer 20 and the interdigital transducer 6, a further intermediate layer 21 can be provided to improve the adhesion and/or to protect the IDTs 6. In the arrangement of FIG. 6, the so-called leaky waves or SSB waves are used.

If the component is a so-called Love mode component, then the liquid traps of FIG. 7 can also be created directly in a waveguide layer 23, which otherwise corresponds to the waveguide layer 16 of FIG. 1, by making trenchlike etched features 22. The thickness of the waveguide layer 23 above the second, parallel basic element having the IDTs 6 without the liquid traps can thus be reduced enough that the same sensitivity of the two basic elements is achieved.

Another method, shown in FIG. 8, for creating liquid traps 17 or trenches 22 for waves of the Love mode type is to apply and then structure a further liquid trap layer 25 above the acoustic waveguide layer 23, optionally also using an additional intermediate layer 21 as an adhesion promoter and/or as an etch stop layer, similarly to the example of FIG. 6. In this way, the replicability of the trench depth is improved.

In all the versions, the formation of liquid traps 17 by providing pits of circular or polygonal cross section or by providing a spongelike surface structure, not shown here, can be done as mentioned above. In all the cases described, a thin metal shielding layer 26, which can be from a few nanometers to 100 nm thick, is provided above the liquid traps in order to shield against unwanted acoustoelectrical interactions between the measurement liquid and the sensor arrangement 1. In the exemplary embodiment of FIG. 8, the intermediate layer 21 can furthermore, especially advantageously, be used simultaneously as an adhesion promoter and etch stop layer and as a shielding layer between the waveguide layer 23 and the liquid traps 22.

The fundamental mode of operation of the sensor arrangement 1 described above will be explained below.

By application of an alternating voltage to the electrodes or transducer prongs 7 of one of the interdigital transducers 6 described above, alternating mechanical stresses are created in the substrate 5 because of the inverse piezoelectric effect, and these stresses result in an acoustic shear wave that runs perpendicular to the interdigital transducers 6 through the substrate 5.

If, when acoustic waveguide layers are used, for instance in a sensor arrangement for acoustic Love mode waves, the shear wave speed in the waveguide layer 16, 23 is less than in the substrate 5, the result is a concentration of the acoustical energy below and in this layer (the so-called waveguide effect). The resultant surface wave type is called a Love wave. These acoustic waveguide modes have an increased sensitivity compared to the general shear modes, but the propagation damping of the wave is also affected by the waveguide layer 16, 23. If the propagation conditions of the acoustic wave change, then the propagation speed and the damping are affected, so that a measurement of these wave parameters provides information about the variables involved.

If a liquid measurement medium is located on a basic sensor element having the interdigital transducers 6, the result is a viscous coupling; that is, a thin film of liquid on the surface of the basic sensor element is forced to go along with the shear oscillations. The effective height of the co-oscillating liquid film (decay length) is directly dependent on the viscosity and the frequency. The viscous coupling causes a decrease in the propagation speed of the acoustic wave and an increase in the wave damping in proportion to the root of the density-viscosity product.

If discontinuities acting as liquid traps 17 are now present on the surface of one of the basic sensor elements, then the propagation speed is reduced by a second influence, which is dependent on the liquid density and on the liquid volume enclosed in the liquid traps 17. The change in propagation speed can be measured for instance if a basic sensor element, for instance with the delay line of FIG. 3 or the reflectors 14 of FIGS. 4 and 5, is used as the frequency-determining member in an oscillator circuit. The change in resonant frequency of such an oscillator is a measure for the change in speed of the wave.

If a basic sensor element having the IDTs 6 is also available that is not exposed to the liquid as a measurement variable, then by mixing two oscillator frequencies, such interference variables as temperature factors can be compensated for, and furthermore the low-frequency signal $\Delta f$ is directly available as an output variable.

FIG. 10 shows a basic exemplary embodiment of a circuit layout for ascertaining the density and viscosity of a measurement liquid, with two oscillator circuits 30 and 31. The oscillator frequency $f_1$ of a basic element having the IDTs 6 and liquid traps 17 in the first oscillator circuit 30 is mixed in a mixer 32 with the oscillator frequency $f_2$ of the oscillator circuit 31 without liquid traps; the mixed frequency $\Delta f$ at the output of a low-pass filter 33 located downstream is, in good approximation, a measure for the liquid density, since the viscous influence acting on both oscillator circuits 30 and 31 is compensated for, as are any further interference variables. The prerequisite here is that the sensitivity to viscous coupling be identical in both basic sensor elements.

The viscosity of the measurement liquid can be ascertained with the circuit arrangement described, using the ascertained density, from the shift in the frequency of the basic sensor element without liquid traps in the oscillator circuit 31, compared to the known frequency when the measurement arrangement is operated without a measurement liquid. Analogously, the change in damping can also be used as a measurement variable.

A further, expanded exemplary embodiment of a circuit arrangement for detecting the measurement variables required is shown in FIG. 11. In this circuit arrangement, there is in addition an oscillator circuit 34 with a measurement path without any passage therethrough of the measurement liquid, so that this measurement path acts as a reference element that is not wetted.

This arrangement is advantageous especially whenever the two sensor elements, wetted with the measurement liquid, for technological reasons lack identical sensitivity to viscous interactions. Also in this arrangement, possible component drifting is made more homogeneous, to improve long-term stability.

From the resonant frequency shifts $\Delta f_1$ and $\Delta f_2$, it is possible on the basis of the layout of FIG. 11, and given a known sensitivity of the components to changes in density and viscosity, to ascertain the liquid density and, using the thus-known liquid density from $\Delta f_2$, the viscosity, as described above. Alternatively, once again the change in damping can be used as a measurement variable.

A third embodiment, not shown in the drawing, has two basic sensor elements, both of which are provided with liquid traps, and one of which is in contact with the measurement liquid while the other is in contact with air. The mixed frequency, obtained here in an analogous way to the exemplary embodiments of FIGS. 9–11, is dependent on the density and the root of the density-viscosity product. The damping difference is thus also the measure for the root of the density-viscosity product, since a slight increase in mass as a result of the measurement liquid in the liquid traps results in only a negligible change in damping.

Thus a damping measurement is absolutely necessary, but it is advantageous that only two completely identical basic sensor elements are necessary, for the same sensitivity, drift and mechanical cross sensitivity.

What is claimed is:

1. A sensor arrangement for ascertaining the density and the viscosity of a liquid, having
an arrangement comprising at least two basic sensor elements, at least one of which can be wetted with the liquid, and having
electro-acoustical transducers (6) in the basic sensor elements for generating and detecting surface acoustic waves with predetermined wave modes, from whose propagation behavior along a measurement path a measure for the density and the viscosity of the liquid can be ascertained, characterized in that
liquid traps (17) for the liquid, which extend in an applicable measurement path, are disposed in a region of at least one of the basic sensor elements, parallel to the direction of propagation of a surface acoustic wave.

2. The sensor arrangement of claim 1, characterized in that
the evaluated surface acoustic waves are horizontally polarized acoustic shear waves of the Love mode type.

3. The sensor arrangement of claim 1, characterized in that
evaluated surface acoustic waves are horizontally polarized acoustic shear waves of the SSBW or leaky wave type.

4. The sensor arrangement of one of claim 1, characterized in that
the electro-acoustical transducers are formed of interdigital transducers (6), disposed on a substrate (5), whose transducer prongs (7) are embodied such that requisite wave modes can be generated with a suitable oscillator frequency.

5. The sensor arrangement of claim 1, characterized in that
each basic sensor element is embodied as a delay line with two interdigital transducers (6a, 6b) and with a propagation or measurement path (13) between the transducers.

6. The sensor arrangement of 1, characterized in that
each basic sensor element is embodied as a two-gate resonator with two side-by-side interdigital transducers (6a, 6b) and respective reflectors (14) located on the outside of the transducers.

7. The sensor arrangement of claim 1, characterized in that
each basic sensor element is embodied as a one-gate resonator with one interdigital transducer (6) and respective reflectors (14) located on the outside of the transducers.

8. The sensor arrangement of claim 1, characterized in that
the liquid traps (17) are formed by trenches or etched features (22) in a suitably structurable layer (20) above the electro-acoustical transducers (6), optionally on an intermediate layer (21).

9. The sensor arrangement of claim 1, characterized in that
the liquid traps (17) are formed by trenches or etched features (22) in a suitably structurable layer (20) above the electro-acoustical transducers (6), optionally with an outer metal shielding (26).

10. The sensor arrangement of claim 1, characterized in that
the liquid traps (17) are formed by trenches or etched features (22) in a suitably structurable layer (20) above the electro-acoustical transducers (6), and that
an intermediate layer (21) located below the transducer and a further acoustic waveguide layer (23), located between the intermediate layer (21) and the electro-acoustical transducers (6), is present.

11. The sensor arrangement of claim 1, characterized in that
the liquid traps (17) are formed by trenches (22) extending parallel to the direction of propagation of an acoustic wave.

12. The sensor arrangement of claim 1, characterized in that
the liquid traps (17) are formed from an arrangement of pits of circular or polygonal cross section or from a spongelike surface structure.

13. A method for ascertaining the density and viscosity of a liquid, having a sensor arrangement of claim 1, characterized in that
with a first oscillator circuit (30), which has a sensor element with liquid traps (17, 22), a first oscillator frequency $f_1$ is generated,
with a second oscillator circuit (31), which has a sensor element without liquid traps, a second oscillator frequency $f_2$ is generated; that
from a mixed frequency $\Delta f$ of the two oscillator frequencies $f_1$ and $f_2$, the density of the liquid is ascertained, and that
from a frequency shift of the second oscillator frequency $f_2$ of the oscillator circuit (31), the viscosity of the liquid is ascertained in a measurement without liquid compared a the measurement with liquid.

14. A method for ascertaining the density and viscosity of a liquid, having a sensor arrangement claim 1, characterized in that
with a first oscillator circuit (30), which has a sensor element with liquid traps (17, 22), a first oscillator frequency $f_1$ is generated; that
with a second oscillator circuit (31), which has a sensor element without liquid traps, a second oscillator frequency $f_2$ is generated; that
with a third oscillator circuit (34), which has a sensor element without liquid traps and without the liquid to be measured, a third oscillator-frequency $f_3$ is generated; that
from a mixed frequency $\Delta f_1$ of the first and third oscillator frequencies $f_1$ and $f_3$, and a mixed frequency $\Delta f_2$ of the second and third oscillator frequencies $f_2$ and $f_3$, the density of the liquid is ascertained, and that
from the mixed frequency $\Delta f_2$, the viscosity of the liquid is ascertained.

15. A method for ascertaining the density and viscosity of a liquid, having a sensor arrangement of claim 1, characterized in that
with a first oscillator circuit, which has a sensor element with liquid traps, a first oscillator frequency $f_1$ is generated; that
with a second oscillator circuit, which has a sensor element without liquid traps and without the liquid to be measured, a second oscillator frequency $f_2$ is generated; that
from a mixed frequency $\Delta f$ of the first and second oscillator frequencies $f_1$ and $f_2$, a measurement signal is ascertained as a function of the density and the root of the density-viscosity product of the liquid; and that
from damping difference of the two oscillator frequencies $f_1$ and $f_2$, a measure for the root of the density-viscosity product is ascertained.

* * * * *